United States Patent [19]

Corley

[11] Patent Number: 4,935,563

[45] Date of Patent: Jun. 19, 1990

[54] PURIFICATION OF CYCLOBUTENOHALOARENES

[75] Inventor: Larry S. Corley, Houston, Tex.

[73] Assignee: Shell Oil Company, Houston, Tex.

[21] Appl. No.: 262,756

[22] Filed: Oct. 26, 1988

[51] Int. Cl.$^5$ .................. C07C 17/38; C07C 17/10
[52] U.S. Cl. ........................ 570/211; 570/206
[58] Field of Search .................. 570/206, 211, 207

[56] References Cited

U.S. PATENT DOCUMENTS

| | | | |
|---|---|---|---|
| 2,564,507 | 9/1948 | Schaeffer | 260/650 |
| 2,654,506 | 9/1948 | Schaeffer | 260/650 |
| 2,908,730 | 10/1959 | Binning et al. | 260/676 |
| 3,539,653 | 11/1970 | Frevel et al. | 260/681.5 |
| 4,401,559 | 8/1983 | Gaillard | 208/262 |
| 4,686,317 | 8/1987 | Quann et al. | 585/860 |

FOREIGN PATENT DOCUMENTS

| | | | |
|---|---|---|---|
| 0031628 | 3/1978 | Japan | 570/211 |
| 213009 | 1/1967 | U.S.S.R. | |
| 734176 | 3/1978 | U.S.S.R. | |

OTHER PUBLICATIONS

Borg et al, "A New Synthesis of Benzuryclobutene" Oct. 1958, p. 283.

Primary Examiner—Werren B. Lone

[57] ABSTRACT

A process is described for purification of a reaction product mixture of cyclobuteno-4-haloarene containing aliphatic halide impurities. The product mixture is contacted with a tertiary amine under conditions effective for conversion of aliphatic halides to soluble species which can be removed from the mixture by extraction. The process can be used, for example, in the recovery of 4-bromobenzocyclobutene from a reaction product mixture containing aliphatic halide by-products such as 1-bromo-2-(2-bromoethyl)benzene.

26 Claims, No Drawings

PURIFICATION OF CYCLOBUTENOHALOARENES

BACKGROUND OF THE INVENTION

This invention relates to the halogenation of cyclobutenoarenes. In one embodiment, the invention relates to recovery of 4-halobenzocyclobutene from a reaction product mixture containing by-product aliphatic halides such as 1-halo-2-(2-haloethyl)benzene.

The four-membered ring of benzocyclobutenes is known to open at elevated temperature to form a very reactive diene which rapidly dimerizes and polymerizes. Molecules containing two or more benzocyclobutene groups are therefore useful as heat-curable thermosetting resins. Also, elastomers or thermoplastics containing benzocyclobutene substituents crosslink on heating. One of the easiest and most useful methods of functionalizing the benzocyclobutene molecule for subsequent production of resins or functionalized polymers is halogenation of the aromatic ring. Bromination with aqueous bromine, for example, can yield 4-bromobenzocyclobutene in over 75% yield. However, a significant proportion of the starting benzocyclobutene (10-15%) reacts with bromine by addition and opening of the four-membered ring to form 1-bromo-2-(2-bromoethyl)benzene.

The simplest method of separating the desired 4-bromo product from the ring-opened dibrominated 1-bromo by-product would appear to be distillation. However, when the product mixture is distilled, even at pressures as low as 400 Pa (3 mm Hg), the distillation is eventually disrupted by HBr formation. HBr formation is also undesirable because of its corrosive effects on down-stream vessels and equipment. As the HBr is formed, the distillate becomes contaminated with o-bromostyrene produced with loss of HBr from the 1-bromo by-product. The problem of HBr formation during distillation can be alleviated somewhat by adding an HBr scavenger such as an epoxy resin to the distillation pot. However, such scavengers are not completely effective (a nonvolatile epoxy resin will not scavenge HBr formed in the column rather than in the pot) and, in any case, they do not solve the problem of o-bromostyrene contamination of the distillate.

It is therefore an object of the invention to provide a method for the recovery of a cyclobutenohaloarene from a reaction product mixture containing by-product halides. In a specific aspect, it is an object of the invention to provide a method for recovering 4-bromobenzocyclobutene from a reaction product mixture containing by-product aliphatic halides without generating large quantities of additional HBr and o-bromostyrene.

SUMMARY OF THE INVENTION

According to the invention, a cyclobutenohaloarene is recovered from a reaction product mixture containing halogenated by-products by a process which includes contacting the crude cyclobutenohaloarene product with a tertiary amine under conditions effective to convert halogenated by-products to soluble species which can then be removed from the mixture by, for example, extraction. In a specific embodiment, the process can be used to remove impurities such as 1-halo-2-(2-haloethyl)benzene from a 4-halobenzocyclobutene reaction product mixture, by heating the reaction product mixture in the presence of a tertiary amine to form water-soluble species, and then extracting the water-soluble species with water.

DETAILED DESCRIPTION OF THE INVENTION

The invention process involves contacting a cyclobutenoarene halogenation product mixture with a tertiary amine. Suitable tertiary amines include substituted and unsubstituted aliphatic amines, including those which can be represented by the formula

in which each R is selected independently from substituted and unsubstituted $C_{1-3}$ alkyl. In general, the most preferred amines will have sufficiently low polar group concentration as to be soluble in the cyclobutenohaloarene and sufficiently low total content of organic groups that any quaternary ammonium salts formed by the reaction of the amine with halogenated impurities are not strong emulsifiers, as the presence of emulsifiers hinders phase separation and removal of excess amine.

A preferred tertiary amine, because of its low cost and low molecular weight, is trimethylamine. The use of trimethylamine requires that the treatment be conducted in a vessel which can withstand pressures generated by heating the trimethylamine above room temperature. Triethylamine and higher trialkylamines can be used but are less preferred because of the tendency of the quaternary salt reaction products to be strong emulsifiers, which can make separation of the amine from the treated cyclobutenohaloarene difficult.

Tertiary amines containing additional polar groups such as hydroxyl are suitable, particularly when it is desirable to avoid elevated pressures. The preferred polar amine is 2-(dimethylamino)ethanol. Highly polar amines such as triethanolamine can be used, but reaction rates will be relatively slow as a result of the limited solubility of such amines in the cyclobutenohaloarene.

The invention purification process involves mixing a crude cyclobutenohaloarene with the chosen amine under suitable conditions for aliphatic halide impurities to be chemically converted by, e.g., quaternization and/or dehydrohalogenation. Such conversion will be promoted by heating the mixture to a temperature within the range of about room temperature to about 180° C., preferably from about 50° C. to about 120° C. It is generally preferred to employ more amine, on a molar basis, than the amount of impurities to be removed. The amount of the amine will generally be within the range of about 1.2 to about 2 moles of amine per mole of impurities to be converted. The amount of amine for efficient conversion can be reduced by, for example, addition of an inorganic base such as sodium hydroxide to the solvent phase.

A sufficient amount of water, or other solvent for the quaternary halide which will be formed, is preferably present in the solution to prevent precipitation of the quaternary halide as a solid phase, which could cause reactor fouling. Although water, because of its availability and demonstrated effectiveness, is the preferred solvent for extraction of the quaternary halide, other solvents for the conversion products but nonsolvents for the cyclobutenohaloarene, such as ethylene glycol, propylene glycol and formamide, for example, can be employed. The progress of the reaction, and the resulting disappearance of known aliphatic halide peaks, can be monitored by gas chromatography or another analytical method. The contacting time will vary with other reaction conditions including temperature, but will continue for a time sufficient to convert at least a portion of the aliphatic halides to soluble species, usually a time of from about 2 to about 24 hours.

Following the reaction, quaternary halide and excess amine can be removed from the organic phase, typically by diluting with water (if necessary) and acidifying to force excess amine into the aqueous phase and then removing the aqueous phase (see Example 2). During the amine treatment step, some of the aliphatic halide impurity will always have been dehydrohalogenated to an unsaturated compound (for example, o-bromostyrene in the case of 1-bromo-2-(2-bromoethyl)benzene). Such unsaturated impurities can be removed from the remaining organic phase by, for example, treatment with an aqueous acid solution of sufficient strength to polymerize or oligomerize the unsaturated impurities or hydrate them to alcohols which are sufficiently less volatile than the cyclobutenohaloarene that separation by distillation is possible (see Example 4). The aqueous acid solution, of course, must not be so strong that it attacks the cyclobutenohaloarene itself at a significant rate. For example, o-bromostyrene can be removed by treatment with 83–85% aqueous sulfuric acid at 40°–60° C. with vigorous stirring. The remaining organic phase can then be distilled for removal of remaining impurities and further purification, if desired, of the 4-bromobenzocyclobutene.

The process of the invention can be employed to purify cyclobutenohaloarenes prepared by any process. Generally, halogenation of cyclobutenoarenes involves contacting the cyclobutenoarene with a halogen source in the presence of a catalyst. For example, U.S. Pat. No. 4,540,763 discloses a method for preparing 4-bromobenzocyclobutene from benzocyclobutene and an excess of pyridinium bromide perbromide, catalyzed with mercuric acetate. Another procedure, published in *Tetrahedron* 21, 245–254 (1965), uses elemental bromine in 95% aqueous acetic acid with an iodine catalyst.

The preferred method for preparing a purified cyclobutenohaloarene according to the invention involves the reaction of a cyclobutenoarene with a halogen source (such as $Br_2$, for example) in the organic phase of a two-phase reaction mixture which also includes an aqueous phase. The reaction is carried out under reaction conditions suitable for electrophilic substitution, generally atmospheric pressure and a temperature of about −80° to about 80° C. As the halogen and cyclobutenoarene react to form a cyclobutenohaloarene, by-product HX migrates into the aqueous phase. The organic phase containing cyclobutenohaloarene and aliphatic halide by-products such as 1-halo-2-(2-haloethyl)benzene can be washed and dried and the cyclobutenohaloarene recovered by the invention purification process.

The following examples illustrate specific embodiments of the invention process for purifying cyclobutenohaloarenes in a manner which avoids generation of large amounts of HBr and unsaturated impurities.

EXAMPLE 1

This example illustrates the use of various amines to purify crude 4-bromobenzocyclobutene (4-bromo BCB) in the absence of added water. Each of three vials was charged with 10 grams of crude 4-bromo BCB (containing 11.5% of 1-bromo-2-(2-bromoethyl)benzene, BBEB) plus 2.5 grams of an amine. The vials were placed in a 95° C. oven and allowed to remain there for 18 hours. The vials were then cooled to room temperature. The contents were mixed with water and acidified. The organic phase was separated from the aqueous phase and analyzed by gas chromatography.

Table 1 shows that treatment with triethylamine reduced the BBEB level to less than 1%. When 2-(dimethylamino)ethanol was used as the amine, BBEB was reduced to levels which were undetectable. Triethanolamine produced little reduction of the BBEB concentation under the experimental conditions, possibly due to solubility problems. In the treated samples, the disappearance of BBEB was accompanied by the appearance of o-bromostyrene.

TABLE 1

| Amine used | Analysis of components in treated material, GC peak area %[b] | | | | | | |
|---|---|---|---|---|---|---|---|
| | BCB | 4-chloro BCB | o-bromo Styrene | 4-bromo o-xylene | 3-bromo BCB | 4-bromo BCB | BBEB |
| (Analysis of starting material) | 7.6 | 0.20 | 0 | 3.12 | 0.90 | 68.8 | 11.5 |
| $(CH_3CH_2)_3N$ | 8.0 | 0.25 | 6.70 | 3.30 | 1.06 | 72.7 | 0.76 |
| $(CH_3)_2NCH_2CH_2OH$ | 7.9 | 0.24 | 7.32 | 3.34 | 1.05 | 73.8 | 0 |
| $(HOCH_2CH_2)_3N$ | 7.7 | 0.25 | 0.55 | 3.16 | 0.95 | 69.8 | 10.6 |

All thrre of the vials contained fairly large amounts of solid deposits at the end of the oven treatment, probably quaternary ammonium salts. These solids dissolved when the contents of the vials were mixed with water.

EXAMPLE 2

This example shows the treatment of crude 4-bromo BCB with aqueous solutions of various amines with stirring under reflux. Crude 4-bromo BCB was treated with mixtures of equal weights of amines and water and stirred under reflux overnight (or longer) as shown in Table 2. The mixtures were then acidified with 20% or 40% aqueous $H_2SO_4$ after amine treatment, and the phases were separated. The organic phase was washed and analyzed by gas chromatography as in Example 1. Results are shown in Table 2.

One can see from Table 2 that the three amines tested showed the same order of effectiveness in the aqueous reflux as in the anhydrous treatment in Table 1. 2-(Dimethylamino)ethanol was slightly more effective than triethylamine, while triethanolamine was low in effectiveness. 2-(Dimethylamino)ethanol is preferred over triethylamine as a treatment agent because the organic and aqueous phases are easier to separate when 2-(dimethylamino)ethanol is used.

TABLE 2

Reflux of mixtures of crude 4-bromobenzocyclobutene (4-bromo BCB) with aqueous amines to remove aliphatic bromine

| Crude 4-bromo BCB, grams | Amines and other reactants | Reaction temp., °C. | Reaction time, hr. | Stirring or Agitation type | Analysis of components in amine-treated crude 4-bromo BCB, GC peak area % | | | | | | |
|---|---|---|---|---|---|---|---|---|---|---|---|
| | | | | | BCB | 4-chloro BCB | o-bromo Styrene | 4-bromo o-xylene | 3-bromo BCB | 4-bromo BCB | BBEB |
| Starting material for following group of 4 experiments: → | | | | | 7.6 | 0.20 | 0 | 3.12 | 0.90 | 68.8 | 11.5 |
| 50 | $(CH_3CH_2)_3N$ (12.5 g) Water (12.5 g) | reflux | 18 | magnetic | 8.1 | 0.26 | 6.13 | 3.36 | 1.05 | 74.0 | 0.25 |
| | | | 40 | | 8.7 | 0.27 | 1.88 | 3.55 | 1.17 | 78.0 | <0.1 |
| 50 | $(CH_3)_2NCH_2CH_2OH$ (12.5 g) Water (12.5 g) | reflux | 18 | magnetic | 7.9 | 0.23 | 4.82 | 3.38 | 1.23 | 73.5 | <0.1 |
| | | | 40 | | 7.9 | 0.26 | 7.65 | 3.37 | 1.13 | 73.7 | 0 |
| 50 | $(HOCH_2CH_2)_3N$ (12.5 g) Water (12.5 g) | reflux | 66 | magnetic | 7.6 | 0.22 | 1.33 | 3.23 | 0.95 | 71.0 | 8.4 |
| 1218 | $(CH_3)_2NCH_2CH_2OH$ (304.5 g) Water (304.5 g) | reflux | 18 | magnetic | 8.2 | 0.25 | 5.57 | 3.40 | 1.02 | 74.8 | <0.1 |
| Starting material for the following experiment: → | | | | | 9.0 | 0.22 | 0 | 1.62 | 1.05 | 71.9 | 11.6 |
| 2837 | $(CH_3)_2NCH_2CH_2OH$ (678 g) Water (709 g) | reflux | 18 | magnetic | 9.5 | 0.27 | 6.33 | 1.70 | 1.06 | 76.8 | 0 |

EXAMPLE 3

This comparative experiment shows the distillation of a crude 4-bromo BCB sample similar to that used in Example 4 below but without treatment with amines or sulfuric acid. One can see from Table 3 below that o-bromostyrene began to form at one point during the distillation and started to accumulate in later cuts, although the starting material contained no o-bromostyrene. Concurrently with the appearance of o-bromostyrene in the distillate, HBr began to form in the system and tended to disrupt the distillation, making further distillation difficult (even though approximately 5% of EPON ® Resin 828 had been added to the material in the pot as an HBr scavenger).

sulfuric acid and 150 grams of water was prepared. This mixture was then added to the flask containing the combined organic phases. Heat was applied in order to bring the temperature of the reaction mixture up to 45°–49° C. with strong stirring. The reaction mixture was kept in this temperature range for 70 minutes with strong stirring (total contact time between organic and acid phases was approximately 150 minutes). The phases were then allowed to separate and the aqueous acid phase was pumped out of the flask. Approximately 150 grams of calcium oxide was added to the organic phase to neutralize any remaining acid.

This mixture could not be filtered through fritted glass filters because "tars" which were formed during the acid treatment clogged the filters. Hence the mix-

TABLE 3

Contents of Distilled Fractions of 4-Bromobenzocyclobutene

| Cut # | Weight % cut | Weight % cumulative | Boiling[a] range, °C. begin | Boiling[a] range, °C. end | Analysis of components GC peak area % | | | | | |
|---|---|---|---|---|---|---|---|---|---|---|
| | | | | | o-xylene | BCB | 4-chloro BCB | o-bromo Styrene | 4-bromo o-xylene | 3-bromo BCB | 4-bromo BCB |
| Starting material:[b] → | | | | | 0.05 | 10.98 | 0.20 | 0 | 0.60 | 0.86 | 68.93 |
| 1 | 17.0 | 17.0 | 164 | 228 | 0.2 | 44.9 | 0.6 | | 0.9 | 1.3 | 51.0 |
| 2 | 8.5 | 25.5 | 228 | 232 | | 3.1 | 0.5 | | 1.7 | 2.4 | 90.4 |
| 3 | 9.2 | 34.7 | 232 | 233 | | 0.3 | 0.3 | | 0.9 | 1.3 | 96.2 |
| 4 | 7.8 | 42.5 | 233 | 216 | | 0.1 | 0.1 | | 0.8 | 1.2 | 96.5 |
| 5 | 8.1 | 50.6 | 216 | 218 | | | | 0.1 | 0.7 | 1.0 | 97.0 |
| 6 | 8.6 | 59.2 | 218 | 219 | | | | 0.1 | 0.2 | 0.3 | 98.4 |
| 7 | 9.0 | 68.2 | 219 | 226 | | | | 0.6 | | 0.1 | 98.2 |

[a]Distillation carried out in a 2.54 cm diameter Oldershaw column with 30 plates at 10:1 reflux ratio. Pressure was 3–6 mm Hg (400–800 Pa). Boiling points are corrected to atmospheric pressure. Fluctuations in boiling point are caused by system pressure fluctuations.
[b]Starting material contained 13.75% (GC peak area) of 1-bromo-2-(2-bromoethyl)benzene (BBEB). No BBEB was detected in any of the distillation cuts.

EXAMPLE 4

This example shows the removal of unsaturated byproducts from a mixture containing 4-bromobenzocyclobutene. The combined organic phases isolated, after acidification, from the last two amine treatment batches in Table 2 were added to a 5-liter round-bottom flask fitted with a paddle stirrer and a heating mantle. A mixture of 850 grams of reagent grade concentrated ture was flash-distilled from the calcium oxide at pressures starting near 400 Pa (3 mm Hg) and ending below 100 Pa. The final pot temperature was approximately 150° C. Table 4 shows GC data for the starting material, the material after acid treatment (but before flash distillation), and the material after flash distillation. One can see from Table 4 that the acid treatment lowered the level of o-bromostyrene in the mixture from 6.1% before treatment to 0.21% after.

TABLE 4

| | GC Analysis of Components in Material | | | | | | |
|---|---|---|---|---|---|---|---|
| | BCB | 4-chloro BCB | o-bromo Styrene | 4-bromo o-xylene | 3-bromo BCB | 4-bromo BCB | BBEB |
| Before acid treatment | 9.1 | 0.26 | 6.10 | 2.21 | 1.04 | 76.2 | 0 |

TABLE 4-continued

| | GC Analysis of Components in Material | | | | | | |
|---|---|---|---|---|---|---|---|
| | BCB | 4-chloro BCB | o-bromo Styrene | 4-bromo o-xylene | 3-bromo BCB | 4-bromo BCB | BBEB |
| After acid treatment but before flash distillation | 5.3 | 0.29 | 0.21 | 2.39 | 1.13 | 81.6 | 0 |
| After flash distillation | 5.4 | 0.30 | 0.21 | 2.52 | 1.19 | 86.2 | 0 |

The flash-distilled material from Table 4 was then distilled through an Oldershaw column under conditions similar to those in Example 3 except for a lower reflux ratio. Distillation data are shown in Table 5. One can see from Table 5 that no o-bromostyrene was formed during the distillation to contaminate the later cuts (although a small amount, not removed by the sulfuric acid treatment, was present in the starting material and was brought over the column with the earlier cuts). No formation of HBr in the column was detected at any time during the distillation and no distillation upsets occurred. This was in spite of the fact that no HBr scavenger was added to the distillation pot as was done in Example 3.

TABLE 5

GC Data on Distilled Fractions of 4-Bromobenzocyclobutene

| | Weight % | | Boiling[a] range, °C. | | Analysis of components in distillation cut, GC peak area % | | | | | | |
|---|---|---|---|---|---|---|---|---|---|---|---|
| Cut # | cut | cumu- lative | begin | end | o-xylene | BCB | 4-chloro BCB | o-bromo Styrene | 4-bromo o-xylene | 3-bromo BCB | 4-bromo BCB |
| | Starting material:[b] → | | | | 0.12 | 5.39 | 0.30 | 0.21 | 2.52 | 1.19 | 86.16 |
| 1 | 8.9 | 8.9 | 142 | 222 | 1.07 | 50.73 | 1.35 | 0.56 | 4.25 | 2.06 | 33.79 |
| 2 | 10.2 | 19.1 | 222 | 223 | | | 0.85 | 0.52 | 5.86 | 2.80 | 88.32 |
| 3 | 10.0 | 29.1 | 223 | 217 | | | 0.39 | 0.27 | 4.20 | 1.97 | 92.86 |
| 4 | 9.8 | 38.9 | 217 | 227 | | | 0.16 | 0.14 | 3.02 | 1.39 | 94.76 |
| 5 | 11.9 | 50.7 | 227 | 221 | | | | | 2.43 | 1.13 | 96.44 |
| 6 | 9.2 | 59.9 | 221 | 228 | | | | | 2.11 | 0.97 | 96.93 |
| 7 | 9.4 | 69.3 | 228 | 221 | | | | | 1.62 | 0.73 | 97.64 |
| 8 | 9.7 | 79.0 | 221 | 220 | | | | | 0.95 | 0.42 | 98.63 |
| 9 | 10.2 | 89.2 | 220 | 217 | | | | | 0.35 | 0.14 | 99.51 |
| 10 | 4.1 | 93.2 | 217 | 216 | | | | | | | 100.00 |

[a]Distillation carried out in a 2.54 cm Oldershaw column with 30 plates at a 2:1 reflux ratio (except for distillation of first half of first cut, which was carried out at 4:1 reflux ratio). Pressure was 3–6 mm Hg (400–800 Pa). Boiling points are corrected to atmospheric pressure. Fluctuations in boiling point are caused by system pressure fluctuations.
[b]Starting material for distillation (flash-distilled batch from Table 4).

I claim:

1. A process for treating a mixture comprising a cyclobutenohaloarene and an aliphatic halide comprising:
   (a) contacting said mixture with a tertiary amine under conditions effective for conversion of at least a portion of the aliphatic halide to a soluble species; and
   (b) providing to said mixture a liquid which is a solvent for said soluble species and a nonsolvent for said cyclobutenohaloarene; and
   (c) removing from the thus-treated mixture a solution of said soluble species.

2. The process of claim 1 in which the cyclobutenohaloarene is 4-halobenzocyclobutene.

3. The process of claim 1 in which the tertiary amine is selected from the group consisting of substituted and unsubstituted aliphatic amines.

4. The process of claim 1 in which the liquid is water.

5. The process of claim 4 in which the tertiary amine is selected from the group consisting of trimethylamine, triethylamine, 2-(dimethylamino)ethanol, triethanolamine, and mixtures thereof.

6. The process of claim 1 in which the tertiary amine comprises at least one of trimethylamine and 2-(dimethylamino)ethanol.

7. The process of claim 6 in which the cyclobutenohaloarene is 4-halobenzocyclobutene and the aliphatic halide comprises 1-halo-2-(2-haloethyl)benzene.

8. The process of claim 7 in which the tertiary amine is present in an amount within the range of about 1.2 to about 2 moles per mole of 1-halo-2-(2-haloethyl)benzene.

9. The process of claim 1 in which said contacting is effected at a temperature within the range of about room temperature to about 180° C.

10. The process of claim 4 in which the water is present in an amount within the range of about 50 to about 200 weight percent, based on the weight of the tertiary amine.

11. The process of claim 1 in which the mixture is a product of reacting a cyclobutenoarene with a bromine source in the presence of a suitable catalyst.

12. A process for preparing a cyclobutenohaloarene comprising the steps of:
   (a) providing a reaction mixture comprising an organic phase and an aqueous phase, the aqueous phase comprising a cyclobutenoarene;
   (b) contacting in the organic phase the cyclobutenoarene and a bromine source under reaction conditions effective for producing a reaction product comprising 4-cyclobutenobromoarene, by-product aliphatic bromide and hydrogen bromide and for migration of the hydrogen bromide into the aqueous phase;
   (c) contacting the remaining organic phase comprising the cyclobutenobromoarene and aliphatic bromide with a tertiary amine under conditions effective for conversion of at least a portion of the aliphatic bromide to a soluble species; and
   (d) removing from the product of step (c) a solution of said soluble species.

13. The process of claim 12 in which the cyclobutenoarene is benzocyclobutene and the cyclobutenohaloarene is 4-halobenzocyclobutene.

14. The process of claim 13 in which the halogen source is $Br_2$.

15. The process of claim 13 in which the aliphatic halide comprises 1-halo-2-(2-haloethyl)benzene.

16. The process of claim 12 in which said contacting of step (c) is effected in the presence of water.

17. The process of claim 13 in which the tertiary amine is selected from the group consisting of substituted and unsubstituted aliphatic amines.

18. The process of claim 13 in which the tertiary amine is selected from the group consisting of trimethylamine, triethylamine, 2-(dimethylamino)ethanol, triethanolamine, and mixtures thereof.

19. The process of claim 13 in which the tertiary amine comprises at least one of trimethylamine and 2-(dimethylamino)ethanol.

20. The process of claim 13 in which the aliphatic amine is present in an amount within the range of about 1.2 to about 2 moles per mole of aliphatic halide.

21. The process of claim 12 in which said contacting is effected at a temperature within the range of about room temperature to about 180° C.

22. The process of claim 21 in which the water is present in an amount within the range of about 50 to about 200 weight percent, based on the weight of the tertiary amine.

23. The process of claim 21 in which said contacting is carried out for a time within the range of about 2 to about 24 hours.

24. The process of claim 15 in which the tertiary amine is present in an amount within the range of about 1.2 to about 2 moles of amine per mole of 1-halo-2-(2-haloethyl)benzene.

25. The process of claim 13 which further comprises
 (e) contacting the remaining organic phase comprising the cyclobutenobromoarene with an aqueous acid solution under conditions effective to convert any unsaturated impurities present to less volatile compounds, and
 (f) removing said less volatile compounds from said 4-bromobenzocyclobutene by distillation.

26. The process of claim 12 in which said contacting of step (c) is carried out at a temperature within the range of about 50° to about 120° C.

* * * * *